Figure 1:
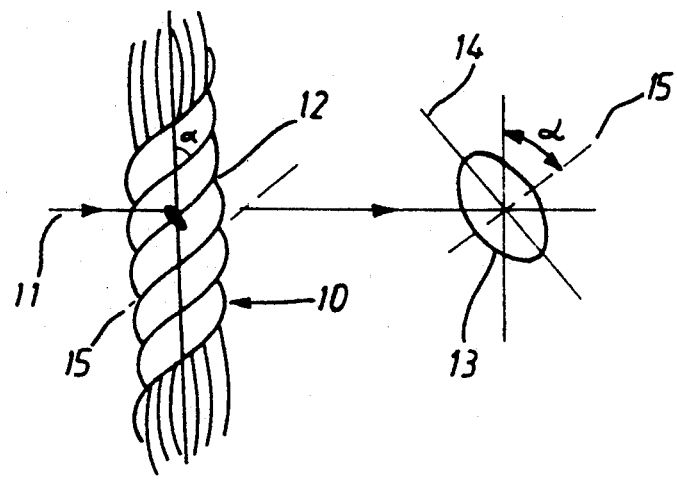

United States Patent
Durand

[11] Patent Number: 5,210,594
[45] Date of Patent: May 11, 1993

[54] PROCESS AND DEVICE FOR MEASURING THE TWIST OF A TEXTILE YARN

[75] Inventor: Bernard Durand, Pfastatt, France

[73] Assignee: Passap Knitting Machines Inc., Salt Lake City, Utah

[21] Appl. No.: 768,933

[22] PCT Filed: Feb. 5, 1991

[86] PCT No.: PCT/FR91/00078
§ 371 Date: Oct. 15, 1991
§ 102(e) Date: Oct. 15, 1991

[87] PCT Pub. No.: WO91/12490
PCT Pub. Date: Aug. 22, 1992

[30] Foreign Application Priority Data
Feb. 6, 1990 [FR] France .................. 90 01393

[51] Int. Cl.⁵ .................................... G01D 11/26
[52] U.S. Cl. .................... 356/429; 250/571; 356/138

[58] Field of Search ............... 356/429, 238, 138, 150, 356/151; 250/227.26, 227.28, 559, 571

[56] References Cited
U.S. PATENT DOCUMENTS
3,985,450 10/1976 Plockl ............................ 356/429
5,030,841 7/1991 Wampfler ....................... 250/571

Primary Examiner—Richard A. Rosenberger
Attorney, Agent, or Firm—Davis, Bujold & Streck

[57] ABSTRACT

The present invention concerns a process and a device for optically measuring the twist of a textile yarn.

The device comprises means (20) for lighting up the yarn (10) by a beam of light (11) to form a spot of light (12) which corresponds to the light diffracted by the surface fibres of the compact core of this yarn. The energy repartition of this spot is then analyzed by means such as a rotary analyzer (27) to define the angle of twist by determination of the maximum of energy in the said spot (12).

4 Claims, 1 Drawing Sheet

PROCESS AND DEVICE FOR MEASURING THE TWIST OF A TEXTILE YARN

The present invention concerns a process for optically measuring the twist of a textile yarn, in which the yarn is lit up by means of a beam of light, to form a spot of light which corresponds to the light diffracted by the surface fibres of the compact core of this yarn.

It also concerns a device for the application of the process for optically measuring the twist of a textile yarn, comprising means for lighting up the yarn by a beam of light, to form a spot of light which corresponds to the light diffracted by the surface fibres of the compact core of this yarn.

Several methods are known for measuring the twist of a textile yarn which constitutes one of the most important characteristics of the yarn. Indeed, most of the mechanical properties and even the accessibility of the reagents, notably colorants during dyeing depend on this fundamental parameter. The twist is determined by the following formula :

$$T tg\alpha/\pi \cdot d$$

where T represents the twist in turns/meter, $\alpha$ the angle of twist and d the diameter of the yarn in meters, insofar as the structure is considered as ideal and corresponds to a traditional model comprising spiral coilings of fibres in superposed layers. In this case, the characteristic angle of the spiral coiling defines the twist. One of the well-known methods is called "measure by simple untwisting".

This method consists in untwisting the yarn until the twist is zero and in noting the number of turns necessary to obtain this untwisting. Although this measure is very simple, in practice, difficulties are met as soon as one moves away from classic carded yarns and the yarn is very irregular, because it is then practically impossible to untwist it evenly and to obtain zero twist.

Indeed, in a very irregular structure, whilst certain parts are untwisted, other parts are still twisted and the untwisting of these means the retwisting in the opposite direction of the parts which have already been untwisted.

In order to offset this drawback, the use of a needle has been suggested; the needle should be slid between the fibres over the distance separating the two clips of the torsion meter. This means working on very short test-pieces of around 2.5 cm to 5 cm at the most. Even in this case, this determination is sometimes very difficult to carry out.

Another well-known method is called "measure by untwisting-retwisting".The principle of the measure by untwisting-retwisting in the opposite direction until the initial length is covered, is based on the working theory whereby the shortening caused by a twist is independent of the direction of the twist. This can only be true in the case of the perfect yarn, a yarn composed of ideal fibres with no "memory" of shape imposed by the twist.

In practice, even as a very result of storing, the position of the fibres in the yarn becomes fixed, and, as a result, there is, inevitably, a certain memory of the shape.

A third well-known method is called "measure by multiple untwistings-retwistings with test correction".

Counter-testing has been suggested on several occasions as a means of aiming at a correct estimation of twist. Determination by counter-testing consists in carrying out an untwisting and a retwisting followed by another untwisting and retwisting in the original direction until the initial length is covered. This measure once again supposes a compensation of the behaviour by untwisting-retwisting in both directions of the twist.

The measure of untwisting-retwisting with quadruple counter-test is a measure for determining the twist which necessitates four successive measures carried out by means of a same meter. To begin with, the test-piece is untwisted then retwisted continuously until it gets back its initial length. It is untwisted by the number of turns necessary to cancel out the twist, then retwisted by the same number of turns necessary for the retwisting in the opposite direction increased by a certain number of turns because of the imperfect symmetry of the operations of untwisting-retwisting, notably of the greater or lesser fixing of the twist on the yarn when the measure is taken.

Another method, which is optical, known as microscopic, consists in measuring the angle of inclination of the coils of fibres in relation to the axis of the yarn, and in calculating the twist T (turns/m), the diameter of the yarn d (m) being known.

This thus implies a yarn made up of successive concentric layers of fibres set out evenly, and also a yarn diameter rigorously defined in a perfectly cylindrical envelope, which is never the case. Moreover, the relatively high variation of the visible section of the yarn means a great number of measures are necessary.

The PARAMONOV method provides a rapid technique for determining the angle of twist based on ar optical method which uses the dispersion to the small angles of the laser beams by the fibres. In order to observe the phenomenon, a narrow laser beam is oriented perpendicularly to the yarn. The rays diffracted by the yarn are collected by a device placed behind the yarn. The angles contained between the central line and each branch corresponding respectively to the component due to the twis& of the fibres situated on the upper edge of the yarn and to that due to the twist of the fibres situated on the lower edge of the yarn, are equal to the angles of inclination of the superficial fibres in relation to the axis on either side of the yarn.

This quick measure for the determination at a particular time of the situation of the fibres at a given point of the yarn only enables one to obtain an approximate value of the superficial twist, even if the determinations are repeated. This measure only gives acceptable results with classic carded yarns manufactured with great care. In reality, there is an error cf principle. Indeed, the dispersion is the fruit of the marginal fibres of the hair structure of the compact core and not of the superficial fibres of the compact core, which means that the results are, generally, marred by mistakes.

Amongst the known methods, there are two categories of approach for the measure of the twist:
  without deformation of the yarn, the angle of inclination is measured by means of an optical device,
  by subjecting the yarn to either an untwisting or a series of untwisting(s)-retwisting(s) according to given conditions: these are the classic mechanical methods.

None of these well-known methods are really satisfactory. The present invention proposes to solve the problem of the measure of the twist in a quick and satisfactory way.

With this aim, the process according to the invention defined in the preamble is characterized in that this spot of light is examined in order to analyse its energy repartition, and in that the angle of twist is defined by determining the direction of the maximum of energy in the spot.

According to a preferred embodiment, the yarn is lit up by means of a monochromatic beam of coherent light virtually perpendicular to the main direction of the yarn.

To determine the direction of the maximum of energy in the spot, the maximal dimension of this spot is preferably determined, the angle of twist being complementary to the angle made by the direction in which the dimension of the spot is maximal with the main direction of the yarn.

In order to find out the direction in which the dimension of the spot is maximal, at least one revolving slot can be used.

According to another embodiment, the direction in which the dimension of the spot is maximal can be sought by means of a matrix of detectors.

According to a variant, the direction in which the dimension of the spot is maximal can be sought by means of a linear bar of detectors and of a fascicle of optical fibres, at one extremity of which the fibres are set out in a crown shape and the other extremity of which has a linear layout of the fibres.

According to another variant, the direction in which the dimension of the spot is maximal can be sought by means of an angle coder.

Also with this aim, the device for the application of this process is characterized in that it comprises means for analysing the energy repartition of this spot of light and for defining the angle of twist by determination of the direction of the maximum of energy in the said spot.

According to a preferred embodiment, it comprises means for finding out the maximal dimension of this spot.

The means for finding out the maximal dimension of the spot of light comprise a rotary analyzer comprising at least one revolving slot.

According to a variant, the means for finding out the maximal dimension of the spot of light comprise a matrix of detectors.

According to another embodiment, the means for finding out the maximal dimension of the spot of light comprise a linear bar of detectors and a fascicle of optical fibres, at one extremity of which the fibres are set out in a crown shape and the other extremity of which has a linear layout of the fibres.

According to another variant, the means for finding out the maximal dimension of the spot of light comprise an angle coder comprising at least one set of discrete detectors set out on a circular line and an electronic circuit to detect the detectors giving the maximal signal.

Figure 2:
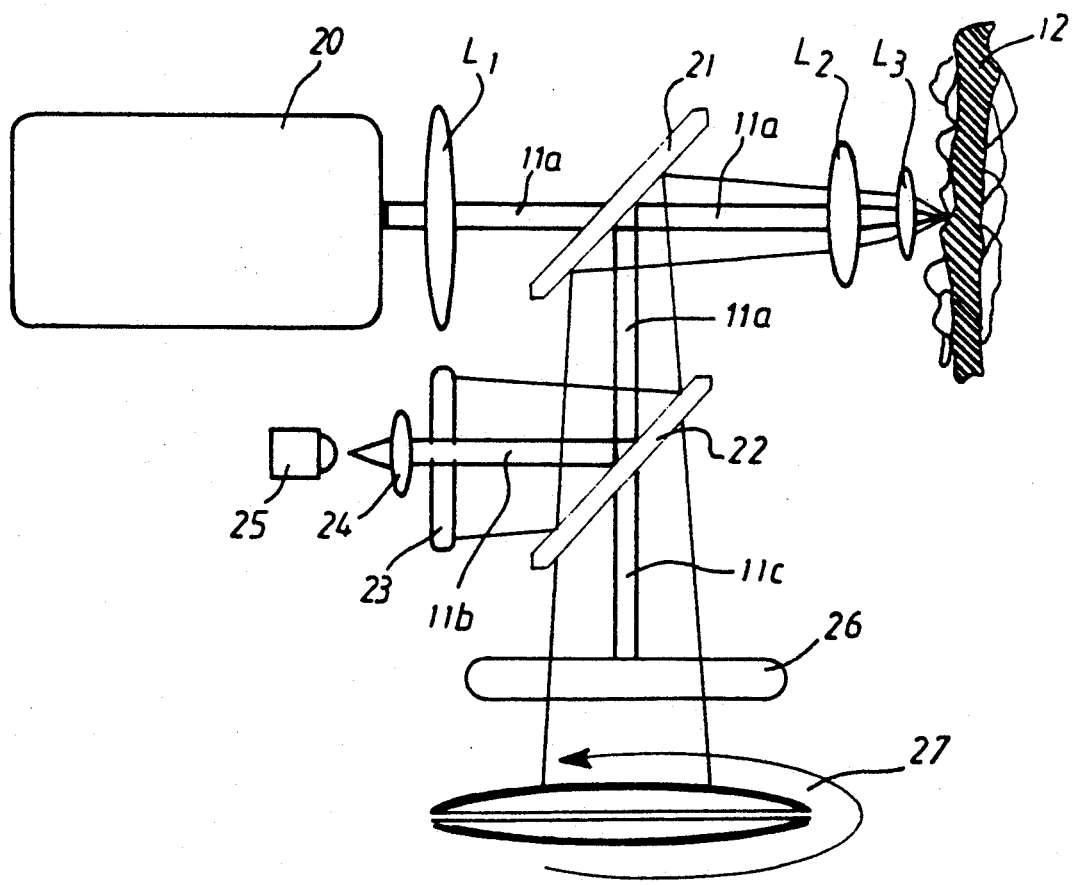

The present invention can be better understood by referring to the description of a preferred embodiment and to the the annexed drawing in which:

FIG. 1 illustrates the form and the layout of a diffraction spot, the analysis of which enables the twist of the yarn to be deduced, and FIG. 2 illustrates a device permitting the measure of the twist of a textile yarn by the process of the invention.

This process is based on the following hypothesis: the yarn has a relatively simple structure, i.e. the idealised structure of the traditional model which has spiral coils of fibres in superposed layers, so that the twist is defined by the characteristic angle of the spiral coiling. The measure itself is based on the theories of diffraction and reflection. The yarn is lit up by means of a beam of light which is, for example, a beam of coherent, monochromatic light, this beam being virtually parallel and narrow. When it reaches the surface fibres of the compact core of the yarn, these diffract the incident light onto the neighbouring fibres, which generates a spot of light on the yarn. The analysis of the energy repartition of this spot of light enables the twist of the yarn to be determined, the main direction of this spot which has an oblong, or in certain cases, virtually elliptical shape, being that which is perpendicular to the fibres.

As shown in FIG. 1, a yarn 10 is lit up by a beam of coherent light 11. The surface fibres of this yarn diffract the light to form a spot of light 12 which can be taken up and projected on a screen to constitute an image 13 which shows an oblong or even elliptical shape. The main axis 14 of the spot 13 is perpendicular to the direction 15 of the yarns. The angle of twist is the angle made by the direction 15 with the axis of the yarn, i.e. the complementary angle of that made by the main axis 14 of the spot of light with the axis of the yarn. The search for the main axis of the spot which is made by an analysis of the energy distribution in the spot, enables the angle of twist $\alpha$ to be determined. FIG. 2 illustrates an embodiment of the device which enables the angle of twist to be measured. It comprises a laser source 20 which emits the beam 11 onto the yarn 12 through optics comprising, for example, three lenses L1, L2 and L3. A semitransparent mirror 21 sends the beam 11a reflected by the yarn 12 to a second semitransparent mirror 22 which divides it into a beam 11b and a beam 11c. The beam 11b is filtered by a filter 23 and transmitted through an optic 24 onto a sensor 25 called a macrostructure sensor. The beam 11c is filtered by a filter 26 and transmitted to a device intended to find out the maximal dimension of the spot of light, which is, for example, a rotary analyzer 27 comprising at least one revolving slot. A sensor 28 called a microstructure sensor picks up the signals transmitted by the rotary analyzer 27.

This rotary analyzer can be replaced by any other appropriate detection device, for example a matrix of detectors, a linear bar of detectors combined with a fascicle of optical fibres, at one extremity of which the fibres are set out in a crown shape and the other extremity of which has a linear layout of the fibres. Another embodiment may have an angle coder comprising at least one set of discrete detectors set out on a circular line an an electronic circuit to detect the detectors giving the maximal signal.

It will be noted that the filter 23 stops the light diffused by the surface fibres, i.e. takes up the image of the impact of the incident beam on the compact core of the yarn, whilst the filter 26 stops the continuous depth, i.e. the light reflected directly by the compact core of the yarn, to take up the trace left by the diffraction of the fibres of the compact core in interaction with the incident beam.

Therefore, the twist can be determined for yarns with cabled fibres such as shown in FIG. 1 by means of the sensor known as a microstructure sensor. The twist of yarns called twist yarns which have intertwined strands, can be determined by the sensor known as a macrostructure sensor.

The present invention is not limited to the embodiments described above but can undergo various modifications obvious for somebody in the profession.

I claim:

1. A process for optically measuring the angle twist of a textile yarn fibers comprising the steps of:
    a) projecting a parallel beam of monochromatic coherent light, circular cross-section having a diameter smaller than the of the yarn onto a lateral surface of the yarn;
    b) sensing the light of the beam after diffraction by the surface fibers of the yarn forms an oblong pattern of diffracted light defining a major axis and a minor axis with the major axis perpendicular to the lengthwise extension of the fibers, the major axis being disposed to an angle to the length of the yarn which is complementary to the angle of twist; and
    c) ascertaining the angle of the major axis to the length of the yarn, thereby to provide a measure of the angle of twist.

2. A process according to claim 1 wherein said angle of the major axis is measured by ascertaining the angle of the maximum dimension of the oblong pattern of reflected light.

3. A process according to claim 2 wherein said maximum dimension is measured by a rotary analyzer having at least one revolving slot through which the diffracted pattern of light passes to a sensor, said angle of the major axis being ascertained by reference to the angle of at least one said revolving slot when aligned with the major axis as detected by the sensor.

4. Apparatus for optically measuring the angle of twist of a textile yarn fibers comprising:
    a) means for projecting a parallel beam of monochromatic coherent light, of circular cross-section having a diameter smaller than that of the yarn, onto a lateral surface of the yarn;
    b) a sensor for sensing the light of the beam after diffraction by the surface fibers of the yarn forms an oblong pattern of diffracted light defining a major axis and a minor axis with the major axis being perpendicular to the lengthwise extension of the fibers, the major axis being disposed to an angle to the length of the yarn which is complementary to the angle of twist; and
    c) means for ascertaining the angle of the major axis to the length of the yarn, thereby to provide a measure of the angle of twist.

* * * * *